(12) United States Patent
Zappala

(10) Patent No.: US 8,685,001 B2
(45) Date of Patent: Apr. 1, 2014

(54) SURGICAL HAIR EVACUATION DEVICE (SHED) AND METHOD OF USE

(76) Inventor: Stephen M. Zappala, Andover, MA (US)

( * ) Notice: Subject to any disclaimer, the term of this patent is extended or adjusted under 35 U.S.C. 154(b) by 649 days.

(21) Appl. No.: 12/557,063

(22) Filed: Sep. 10, 2009

(65) Prior Publication Data

US 2010/0249755 A1 Sep. 30, 2010

Related U.S. Application Data

(60) Provisional application No. 61/163,126, filed on Mar. 25, 2009, provisional application No. 61/240,682, filed on Sep. 9, 2009.

(51) Int. Cl.
*A61M 1/00* (2006.01)

(52) U.S. Cl.
USPC ............ 604/540; 604/8; 604/9; 604/249; 604/288.03; 604/537; 604/543; 604/544; 623/23.64; 623/23.65; 623/23.68; 623/23.7; 137/854; 137/315.24

(58) Field of Classification Search
USPC ........................ 604/540, 543, 544
See application file for complete search history.

(56) References Cited

U.S. PATENT DOCUMENTS

| | | | |
|---|---|---|---|
| 4,031,618 A | 6/1977 | Manfield | |
| 4,400,168 A | 8/1983 | Buechel et al. | |
| 4,692,140 A * | 9/1987 | Olson | 604/40 |
| 4,813,926 A * | 3/1989 | Kerwin | 604/118 |
| 4,843,717 A | 7/1989 | Crane | |
| 5,012,576 A * | 5/1991 | Johannesson | 30/29.5 |
| 5,083,558 A * | 1/1992 | Thomas et al. | 128/202.12 |
| 5,724,736 A | 3/1998 | Smith | |
| 6,086,587 A * | 7/2000 | Hawk | 606/53 |
| 6,638,240 B2 | 10/2003 | Fassuliotis | |
| 7,076,878 B2 * | 7/2006 | Degregorio, Jr. | 30/133 |
| 2002/0108255 A1 | 8/2002 | Degregorio, Jr. | |
| 2008/0250649 A1 | 10/2008 | Spigai | |

FOREIGN PATENT DOCUMENTS

| | | |
|---|---|---|
| DE | 298 12 458 | 10/1999 |
| FR | 1185730 | 8/1959 |

* cited by examiner

*Primary Examiner* — Tatyana Zalukaeva
*Assistant Examiner* — Ilya Treyger
(74) *Attorney, Agent, or Firm* — Brian M. Dingman; Dingman IP Law, PC

(57) ABSTRACT

A device and method for the removal and disposal of transected hair from the body of a patient in an operating room or other sterile location. The hand-held device is single-use, latex-free, sterile-packaged, non-conductive, fully disposable and comprises a hollow handle with a projecting wand ending in an enlarged distal tip. The other end of the hollow handle opposite the enlarged distal tip is connected to a vacuum source, such as the one readily available in most operating rooms, via flexible tubing. When the wand and the enlarged distal tip are passed over transected hair, the hair is suctioned into the hand-held device. The hand-held device includes a particulate filter to prevent the suctioned hair from entering the vacuum system, one or more internal circumferential ribs to create a turbulent flow within the handle, a reservoir to collect transected hair, and venturi apertures to regulate the suction pressure.

12 Claims, 6 Drawing Sheets

SURGICAL HAIR EVACUATION DEVICE (SHED) AND METHOD OF USE

CROSS-REFERENCE TO RELATED APPLICATIONS

This application claims priority to U.S. Provisional Patent Application Ser. No. 61/163,126, entitled "Hand Operative Surgical Suction System (HOSSS) and Method of Use," filed on Mar. 25, 2009 and U.S. Provisional Patent Application Ser. No. 61/240,682 entitled "Surgical Hair Evacuation Device (SHED) And Method Of Use" filed on Sep. 9, 2009. The entire contents of both of the priority applications are expressly incorporated by reference herein.

FIELD OF THE INVENTION

The invention relates to an apparatus for effecting cleaning procedures on body parts in preparation for medical procedures, and in particular, to the sanitary removal and disposal of transected hair prior to surgery or diagnostic examination.

BACKGROUND OF THE INVENTION

A sterile surgical environment is integral to both patient safety and clinical outcomes. The initial preparation of the surgical site requires the removal of any body hair through a gentle shaving of the skin. The transected hair is subsequently accumulated and gathered for removal in order to prepare for topical, cutaneous sterilization. Conventional methods of cut-hair removal are not standardized and remain a variable when one considers infection rates within and between medical centers. The cut-hair removal is routinely performed with a manual, mechanical sweeping motion or with the adhesive side of surgical tape. The adhesive may possibly be contaminated and hair removal may not be complete, potentially increasing the risk factors for surgical infection. An increasing number of patients have developed skin sensitivities or allergies to either the adhesive or to the tape itself. Moreover, the hair may possibly be contaminated with blood, urine, or other bodily fluids and thus may increase exposure to contaminated materials to the ancillary medical staff, such as the risk of exposure to hepatitis, human immunodeficiency virus (HIV), and Methicillin-resistant Staphylococcus aureus (MRSA). There is a need in the art, then, for an improved device and method for the sanitary removal and disposal of transected hair from a patient prior to the introduction of medical procedures.

SUMMARY OF THE INVENTION

The inventive surgical hair evacuation device (SHED) is a hand-operative, surgical suction system that provides a novel device and method for the removal and disposal of transected hair from the body of a patient in an operating room or other sterile location. The invention may be accomplished with a single-use, latex-free, sterile-packaged, non-conductive, and fully disposable system comprising a hollow hand-held device with a projecting wand that terminates in an enlarged, widened distal tip. The wand may have a variable length. In alternate embodiments, the invention may be accomplished without the wand, such that the widened distal tip is coupled directly to the handle of the device.

The other end of the hand-held device, opposite the enlarged distal tip, is connected to a vacuum source, such as the one which is readily available in most operating rooms, via flexible tubing. When the enlarged distal tip is passed over transected hair, the hair is suctioned into the hand-held device. The hand-held device includes a particulate filter to prevent the suctioned hair from entering the vacuum system and further includes venturi apertures to selectively regulate the suction or vacuum pressure. In addition, the hand-held device includes one or more interior concentric, circumferential ribs, preferably arranged in a spiral pattern. The ribs, together with the vacuum, create a turbulent flow inside the hand-held device, such that the transected hair is deposited in the interior of the handle, thereby facilitating hair collection and removal. The handle may further comprise a hemispherical reservoir for collecting the transected hair and a set of caps for sealing the device at both ends after the hair removal is completed. Once sealed, the handle serves as a closed reservoir to facilitate disposal of the collected particulate matter, minimizing the risk of potential contamination.

The inventive system minimizes exposure of potentially contaminated materials and fluids. The device gathers hair by suction from the operating site and prevents these products from airborne dispersion and possible contamination of either the surgical site or potentially the subsequent surgical procedure.

In an embodiment, the invention provides a hand-operative surgical suction system for removing transected hair debris from a patient, for use with a surgical vacuum system, comprising a hand-held device comprising a hollow handle, the handle comprising an inlet, a filter downstream of the inlet to filter out hair and other particulates, an outlet downstream of the filter, one or more internal ribs adapted to create a turbulent flow within the handle; an enlarged tip, where the enlarged tip defines an opening larger than the opening in the inlet; and a distal section coupled at a first end to the handle proximate the inlet and coupled at the opposite end to the enlarged tip. The invention may also include flexible tubing leading from the outlet of the handle to the surgical vacuum system.

In an aspect, the hand-operative surgical suction system further comprises an adapter on one or both ends of the tubing. In another aspect, the enlarged tip defines a generally triangular opening. In yet another aspect, the handle further comprises one or more venturi openings leading to the inner hollow area, where these openings can be selectively blocked by the user to control the suction at the tip. In an additional aspect, the intersection of the distal section and the handle defines a tip angle, and the tip angle is configurable by the user.

In an aspect, the hand-operative surgical suction system further comprises a hollow wand, where one end of the wand is coupled to the handle proximate the inlet, and the distal end of the wand is coupled to the distal section. In an additional aspect, the intersection of the wand and the distal tip define a wand angle. In another aspect, the wand angle is configurable by a user. In yet another aspect, the filter is a HEPA filter.

In an aspect, the handle comprises a reservoir adapted to contain the transected hair debris. In an additional aspect, the internal ribs are arranged in a generally concentric spiral pattern.

In another embodiment, the invention provides a method for removing transected hair debris from a patient, for use with a surgical vacuum system, the method comprising the steps of: (1) providing a hand-held device comprising a hollow handle and a hollow wand, the wand ending in an enlarged tip that defines an opening larger than the opening in the wand, the handle including a filter to filter out hair and other particulates, an outlet downstream of the filter, and one or more internal ribs adapted to create a turbulent flow within the handle; (2) providing flexible tubing leading from the outlet of the handle to the surgical vacuum system; and (3) passing the tip over the transected hair, to remove the hair by vacuum and retain it inside the hand-held device.

In an aspect, the handle further comprises one or more venturi openings leading to the inner hollow area, and the method further comprises the step of controlling the suction at the tip by selectively blocking one or more of the venturi openings. In another aspect, the method further comprises the step of sealing the hand-held device prior to disposal.

In an additional embodiment, the invention provides a hand-operative surgical suction system for removing transected hair debris from a patient, for use with a surgical vacuum system, comprising a hand-held device comprising a hollow handle comprising an inlet, a filter downstream of the inlet to filter out hair and other particulates, an outlet downstream of the filter, and one or more internal ribs adapted to create a turbulent flow within the handle; a hollow wand coupled to the handle proximate the inlet; an enlarged tip defining an opening larger than the opening in the inlet; a hollow distal section coupled to the wand at a first end and to the enlarged tip at the opposite end, and wherein the intersection of the wand and the distal section defines a wand angle; and flexible tubing leading from the outlet of the handle to the surgical vacuum system.

In an aspect, the handle further defines one or more venturi openings leading to the inner hollow area, and these openings can be selectively blocked by the user to control the suction at the tip. In an additional aspect, the internal ribs are arranged in a generally concentric spiral pattern. In another aspect, the invention further comprises one or more caps for sealing the handle prior to disposal.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS OF THE INVENTION

Figure 1:
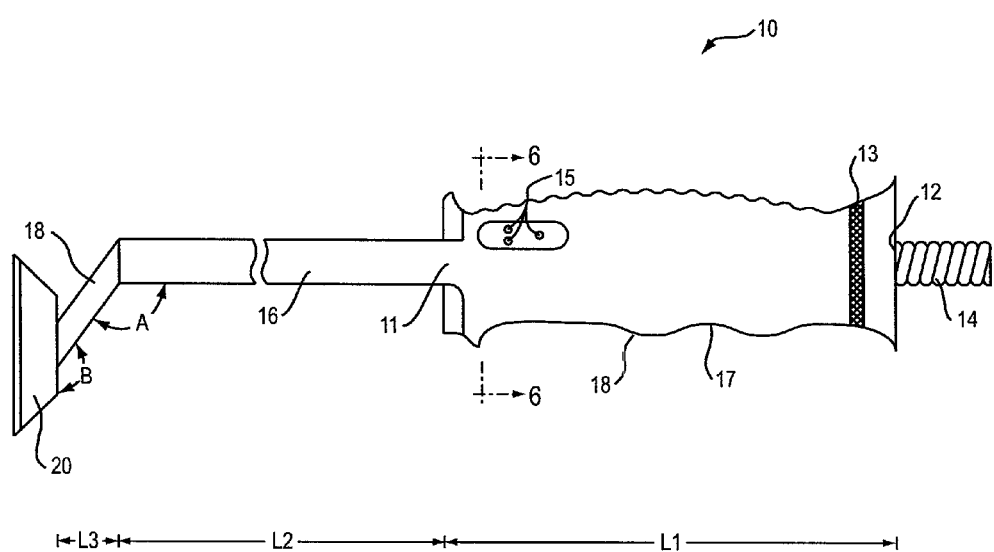
FIG. 1 is a schematic side view of a hand-held device for an inventive hand-operated surgical suction and hair evacuation system, according to a preferred embodiment of the invention.
Figure 2A:
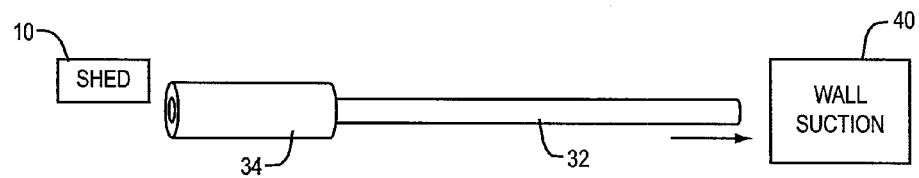
FIG. 2A is a schematic side view of an adapter and suction tubing of the hand-operated surgical suction and hair evacuation system, used with the hand-held device of FIG. 1.

In a preferred embodiment, the surgical hair evacuation device (SHED) comprises hand-held device 10, shown in FIG. 1, and suction tubing 32 with adapter 34, shown in FIG. 2A. The hand-held device 10, suction tubing 32, and adapter 34 are preferably non-conductive, single-use, latex-free, packaged sterile, and fully disposable.

With further reference to FIG. 1, in a preferred embodiment, hand-held device 10 comprises hollow molded plastic vacuum suction handle 17, male fitting 14, wand 16, distal section 18, and enlarged tip 20. Handle 17 is open at both ends, and includes an inlet 11 to, and an outlet 12 from, the hollow interior of handle 17. As shown in FIG. 1, wand 16 is coupled to handle 17 proximate inlet 11, and male fitting is coupled to handle 17 proximate outlet 12.

Distal section 18 may be straight or angled relative to wand 16. In a preferred embodiment, and as shown in FIG. 1, distal section 18 may be positioned at wand angle A from about 90 degrees to about 180 degrees relative to wand 16. In alternate embodiments, distal section 18 may be coupled to wand 16 through the use of an adjustable joint, to allow the user to set a desired wand angle.

Figure 3:
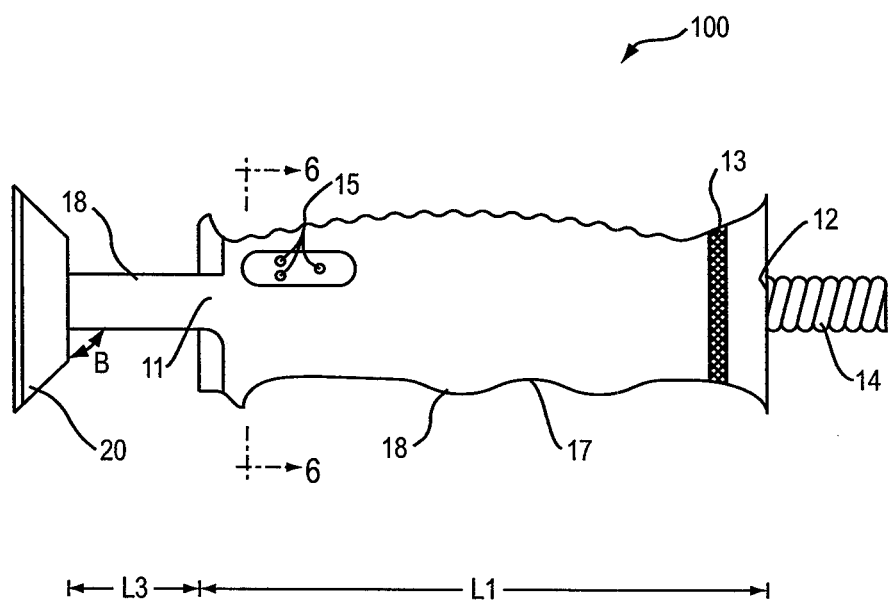
FIG. 3 is a schematic side view of a hand-held device for an inventive hand-operated surgical suction and hair evacuation system, according to an additional embodiment of the invention.

Enlarged tip 20 may be straight or angled relative to distal section 18. In a preferred embodiment, and as shown in FIGS. 1 and 3, enlarged tip 20 may be positioned at tip angle B from about 0 degrees to about 180 degrees relative to distal section 18. In alternate embodiments, distal section 18 may be coupled to wand 16 through the use of an adjustable joint, to allow the user to set a desired tip angle.

In an alternate embodiment, and as shown in FIG. 3, the distal section 18 of hand-held device 100 may be coupled directly to suction handle 17 proximate inlet 11, eliminating wand 16.

In a preferred embodiment, suction handle 17 measures approximately 10 centimeters in length, shown as reference L1 in FIGS. 1 and 3, wand 16 varies in length from approximately 1 centimeter to 15 centimeters in length, shown as reference L2 in FIG. 1, and preferably in lengths of 1 centimeter, 5 centimeters, and 10 centimeters, and distal section 18 measures approximately 2 centimeters in length, shown as reference L3 in FIGS. 1 and 3.

As shown in FIGS. 1 and 3, distal section 18 ends in an enlarged tip 20 that defines an enlarged open area as compared to the diameter of distal section 18 and inlet 11. In a preferred embodiment, enlarged tip 20 is a 3 centimeter triangular vacuum tip, although other sizes and shapes could be used, including but not limited to circular, rectangular or oblong.

Figure 4:
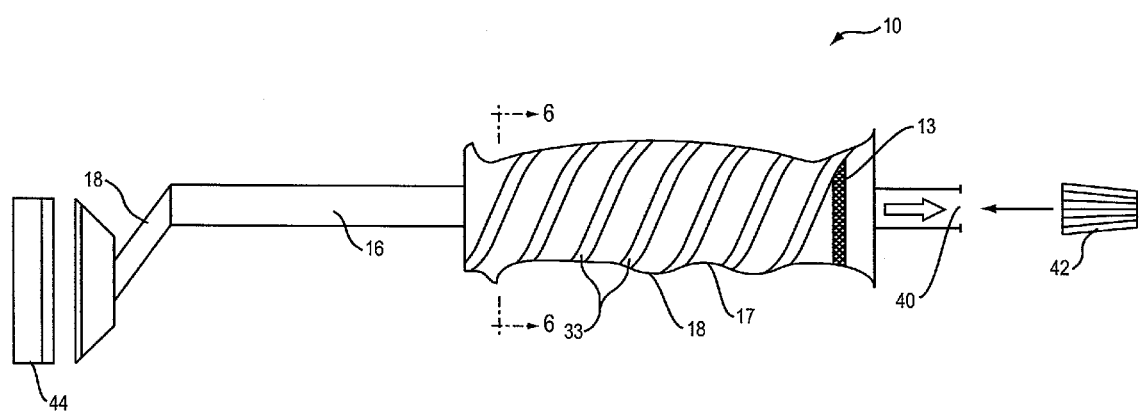
FIG. 4 is a cross-sectional side view of the hand-held device of FIG. 1.
Figure 5:
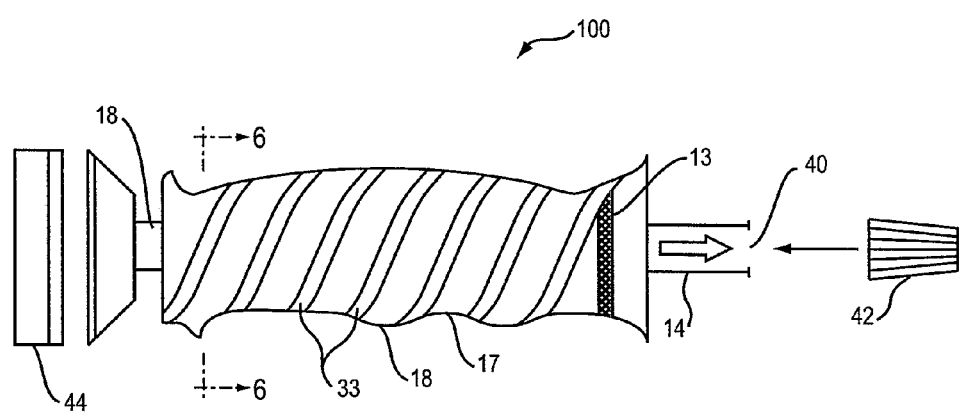
FIG. 5 is a cross-sectional side view of the hand-held device of FIG. 3.

With further reference to FIGS. 1 and 3, and as shown in FIGS. 4 and 5, in a preferred embodiment hollow molded plastic vacuum suction handle 17 is ergonomically designed and comprises filter 13, reservoir 18, one or more internal circumferential ribs 33, and one or more venturi suction regulator apertures 15. Filter 13 collects the aspirated elements in the suction handle 17 and prevents any hair products from entering the suction tubing or the vacuum container, and is preferably a high-efficiency particulate air (HEPA) filter or the equivalent. The one or more apertures 15 are superiorly positioned on the suction handle 17, to allow thumb control of the suction pressure. Apertures 15 are preferably about 5 millimeters in diameter each. As further shown in FIGS. 1 and 3, one end of suction handle 17 is coupled to a male fitting 14 proximate outlet 12 that couples to suction tubing 32 via adapter 34. In a preferred embodiment, the interior of handle 17 includes a reservoir 18 for the collection of transected hair. Reservoir 18 is located towards the bottom of the handle, and in a preferred embodiment, has a generally hemispherical shape. In addition, as shown in FIGS. 4 and 5, caps 42 and 44 may be used to seal device 10 or 100 at both ends for disposal.

Figure 6:
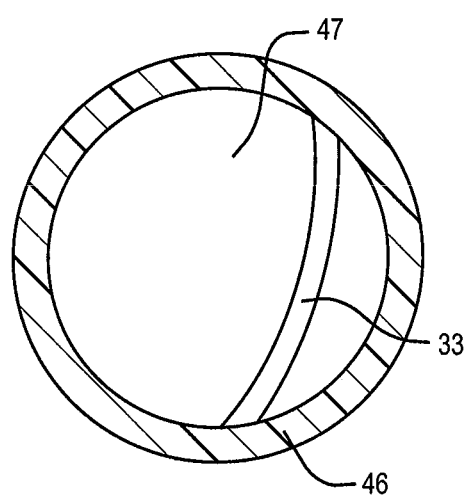
FIG. 6 is an interior view of the handle of FIGS. 1 and 3, taken at line 6-6.

As shown in FIGS. 4 and 5, and with reference to FIG. 6, in a preferred embodiment, suction handle 17 includes one or more interior concentric, circumferential ribs 33, preferably arranged in a spiral pattern. The ribs 33, together with the vacuum, create a turbulent flow within cavity or lumen 47 of suction handle 17, such that the transected hair is deposited in the interior of the handle, preferably in reservoir 18, thereby facilitating hair collection and removal. FIG. 6 provides a view of the interior cavity or lumen 47 of handle 17 along line 6-6 of FIGS. 1 and 3. As shown in FIG. 6, ribs 33 are located on the interior of the handle wall 46.

Figure 2B:
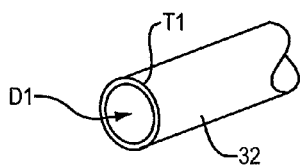
FIG. 2B is a perspective view of the suction tubing of FIG. 2A, showing the interior of the suction tubing.

As shown in FIGS. 2A and 2B, suction tubing 32 is preferably standard tubing, approximately 2 meters in length, with an inner diameter, labeled as reference D1, of 6 millimeters and a wall thickness, labeled as reference T1, of approximately 1 millimeter, and will resist collapse up to a pressure of 20 inches Mercury vacuum.

Figure 2C:
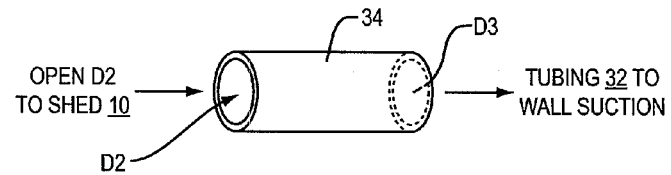
FIG. 2C is a perspective view of the adapter of FIG. 2A, showing the interior of the adapter.

With reference to FIGS. 2A and 2C, one end of suction tubing 32 is coupled to an adapter 34 that is configured to mate with suction handle 17 at fitting 14. In a preferred embodiment, adapter 34 is approximately 4 centimeters in length, and has a diameter, labeled as reference D2, of 1.5 centimeters at the end that mates with suction handle 17 at fitting 14, and narrows to a diameter, labeled as reference D3, of 1.3 centimeters at the end that mates with suction tubing 32.

With reference to FIG. 2A, the opposite end of suction tubing 32 couples to the vacuum source 40, which may be the in-wall suction typically available in most operating rooms.

The entire system, including the hand-held device 10, adapter 34 and suction tubing 32, is a closed system which is disposed in biohazard waste after aspiration, thus minimizing risks for potential exposure or contamination.

The particular construction, materials and dimensions described herein are not limitations of the invention, as other constructions can accomplish the invention described herein.

Although specific features of the invention are shown in some figures and not others, this is for convenience only, as some features may be combined with any or all of the other features in accordance with the invention.

Recitation ranges of values herein are merely intended to serve as a shorthand method of referring individually to each separate value falling within the range, unless otherwise indicated herein, and each separate value is incorporated into the specification as if it were individually recited herein.

The use of any and all examples, or exemplary language (e.g., "such as") provided herein, is intended merely to better illustrate the invention and does not pose a limitation on the scope of the invention.

A variety of modifications to the embodiments described herein will be apparent to those skilled in the art from the disclosure provided herein. Thus, the invention may be embodied in other specific forms without departing from the spirit or essential attributes thereof.

What is claimed is:

1. A hand-held and hand-operative surgical suction system for removing transected hair debris from a patient, for use with a surgical vacuum system, comprising:
   a hollow molded plastic handle that has two opposed ends and that defines an open interior volume bounded by an outer wall that has an interior wall surface;
   a plurality of ribs integrally formed in the outer wall, located and spaced along the interior surface of the wall, and projecting into the interior volume;
   an inlet opening defined in the outer wall at one end of the handle and fluidly coupled to the handle interior volume;
   a hollow conduit fluidly coupled to the inlet opening;
   a tip fluidly coupled to the hollow conduit, the tip defining an opening that is larger in area than the opening of the conduit;
   an outlet opening defined in the outer wall at the other end of the handle, fluidly coupled to the handle interior volume, and constructed and arranged to be fluidly coupled to a vacuum source;
   a flow-through particulate filter located in the interior volume of the handle downstream of the inlet opening and proximate the outlet opening and arranged such that air pulled by the vacuum into the tip, through the conduit, through the inlet opening, through the interior volume of the handle and expelled from the handle through the outlet opening passes through the filter;
   wherein the interior of the handle is constructed and arranged such that air flowing therethrough from the inlet opening to the filter passes through the handle interior volume, where the ribs contribute to turbulent flow in the handle volume;
   wherein the outer wall of the handle defines one or more small apertures that are constructed and arranged to be covered and uncovered by a portion of the user's hand, to provide user control of air flow through the handle interior volume; and
   wherein the outer wall of the handle is closed except for the inlet opening, the outlet opening and the small apertures.

2. The surgical suction system of claim 1 further comprising flexible tubing leading from the outlet opening of the handle to the surgical vacuum system.

3. The surgical suction system of claim 2 further comprising an adapter on one or both ends of the tubing.

4. The surgical suction system of claim 1 wherein the tip defines a generally triangular opening.

5. The surgical suction system of claim 1, where the conduit is constructed and arranged such that the angle of the conduit relative to the handle is configurable by a user.

6. The surgical suction system of claim 1, further comprising a hollow wand located between and fluidly coupled to the tip and the conduit.

7. The surgical suction system of claim 6 wherein the wand is constructed and arranged such that the angle of the wand relative to the conduit is configurable by a user.

8. The surgical suction system of claim 1 wherein the filter is a HEPA filter.

9. The surgical suction system of claim 1, wherein the handle interior further comprises a reservoir adapted to contain the transected hair debris.

10. The surgical suction system of claim 1, wherein the internal ribs are arranged in a generally concentric spiral pattern.

11. The surgical suction system of claim 1, further comprising two caps, the caps constructed and arranged to fluidly close the inlet and outlet openings so as to seal the interior volume of the handle prior to disposal.

12. A hand-held and hand-operative surgical suction system for removing transected hair debris from a patient, for use with a surgical vacuum system, comprising:
   a hollow molded plastic handle that has two opposed ends and that defines an open interior volume bounded by an outer wall that has an interior wall surface, wherein the handle interior defines a reservoir adapted to contain the transected hair debris;
   a plurality of ribs integrally formed in the outer wall, located and spaced along the interior surface of the wall, and projecting into the interior volume, wherein the internal ribs are arranged in a generally concentric spiral pattern;

an inlet opening defined in the outer wall at one end of the handle and fluidly coupled to the handle interior volume;

a hollow conduit fluidly coupled to the inlet opening, where the conduit is constructed and arranged such that the angle of the conduit relative to the handle is configurable by a user;

a tip fluidly coupled to the hollow conduit, the tip defining an opening that is larger in area than the opening of the conduit;

a hollow wand located between and fluidly coupled to the tip and the conduit, wherein the wand is constructed and arranged such that the angle of the wand relative to the conduit is configurable by a user;

an outlet opening defined in the outer wall at the other end of the handle, fluidly coupled to the handle interior volume, and constructed and arranged to be fluidly coupled to a vacuum source;

flexible tubing leading from the outlet opening of the handle to the surgical vacuum system, and an adapter on one or both ends of the tubing;

a flow-through HEPA particulate filter located in the interior volume of the handle downstream of the inlet opening and proximate the outlet opening and arranged such that air pulled by the vacuum into the tip, through the conduit, through the inlet opening, through the interior volume of the handle and expelled from the handle through the outlet opening passes through the filter;

two caps, the caps constructed and arranged to fluidly close the inlet and outlet openings so as to seal the interior of the handle prior to disposal;

wherein the interior of the handle is constructed and arranged such that air flowing therethrough from the inlet opening to the filter passes through the handle interior volume, without meeting obstructions upstream of the filter other than the ribs, which contribute to turbulent flow in the handle volume;

wherein the outer wall of the handle defines one or more small apertures that are constructed and arranged to be covered and uncovered by a portion of the user's hand, to provide user control of air flow through the handle interior volume; and wherein the outer wall of the handle is closed except for the inlet opening, the outlet opening and the small apertures.

\* \* \* \* \*